US012797366B2

(12) United States Patent
Nagarkatti et al.

(10) Patent No.: US 12,797,366 B2
(45) Date of Patent: Nov. 17, 2026

(54) IMMUNE CB1 ACTIVATION FOR OBESITY THERAPY

(71) Applicant: University of South Carolina, Columbia, SC (US)

(72) Inventors: Prakash Nagarkatti, Columbia, SC (US); Kathryn Miranda, Columbia, SC (US); Mitzi Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 17/242,559

(22) Filed: Apr. 28, 2021

(65) Prior Publication Data

US 2021/0401805 A1 Dec. 30, 2021

Related U.S. Application Data

(60) Provisional application No. 63/045,447, filed on Jun. 29, 2020.

(51) Int. Cl.

| | |
|---|---|
| ***A61P 3/04*** | (2006.01) |
| ***A61K 31/00*** | (2006.01) |
| ***A61K 31/4155*** | (2006.01) |
| ***A61K 31/4439*** | (2006.01) |
| ***A61K 31/454*** | (2006.01) |
| ***A61P 29/00*** | (2006.01) |

(52) U.S. Cl.

CPC ...... *A61K 31/4155* (2013.01); *A61K 31/4439* (2013.01); *A61K 31/454* (2013.01); *A61K 31/658* (2023.05); *A61P 3/04* (2018.01); *A61P 29/00* (2018.01)

(58) Field of Classification Search

CPC .............. A61K 31/352; A61K 31/4439; A61K 31/454; A61K 31/4155; A61P 29/00; A61P 3/04

See application file for complete search history.

(56) References Cited

PUBLICATIONS

Pertwee RG Tocris Bioscience Scientific Review Series 2010, https://resources.tocris.com/pdfs/literature/reviews/cannabinoid-receptor-ligands-review-2010.pdf (Year: 2010).*

Yadav MR et al. Advances in patented CB1 receptor antagonists for obesity. Pharm. Pat. Anal. 2018 7(5), 169-173 (Year: 2018).*

Miranda K et al. Cannabinoid Receptor 1 Blockade Attenuates Obesity and Adipose Tissue Type 1 Inflammation Through miR-30e-5p Regulation of Delta-Like-4 in Macrophages and Consequently Downregulation of Th1 Cells. Front. Immunol. 2019 10:1049 (Year : 2019).*

Jourdan T et al. Developmental Role of Macrophage Cannabinoid-1 Receptor Signaling in Type 2 Diabetes. Diabetes 2017;66(4): 994-1007 (Year: 2017).*

Novobrantseva TI et al. Systemic RNAi-mediated Gene Silencing in Nonhuman Primate and Rodent Myeloid Cells. Mol Ther Nucleic Acids. 2012 1(1): e4 (Year: 2012).*

Sou K et al. Bone marrow-targeted liposomal carriers. Expert Opin Drug Deliv. 2011 8(3): 317-328 (Year: 2011).*

Howlett AC et al. CB1 & CB2 Receptor Pharmacology. Adv Pharmacol. 2017; 80: 169-206 (Year: 2017).*

Murphy T et al. Targeting the Endocannabinoid CB1 Receptor to Treat Body Weight Disorders: A Preclinical and Clinical Review of the Therapeutic Potential of Past and Present CB1 Drugs. (Biomolecules. Jun. 4, 2020;10(6):855 1-43) (Year: 2020).*

Lau BK et al. Endocannabinoid modulation of homeostatic and non-homeostatic feeding circuits. (Neuropharmacology 2017 124 38-51) (Year: 2017).*

Tarragon E et al. Role of Endocannabinoids on Sweet Taste Perception, Food Preference, and Obesity-related Disorders. (Chemical Senses, 2018 43(1) 3-16) (Year: 2018).*

* cited by examiner

*Primary Examiner* — Karen A. Canella
*Assistant Examiner* — John J Skoko, III
(74) *Attorney, Agent, or Firm* — Douglas L. Lineberry; Maynard Nexsen PC

(57) ABSTRACT

Described herein are functional CB1 signaling in immune cells is necessary to dampen HFD-induced microglia/macrophage-mediated neuroinflammation and reduce obesity, targeting immune CB1 receptors constitutes a novel therapeutic modality to lessen Diet-Induced Obesity, and circumvent adverse side effects of CB1 antagonist or neuronal CB1 agonist treatment.

4 Claims, 7 Drawing Sheets

IMMUNE CB1 ACTIVATION FOR OBESITY THERAPY

STATEMENT REGARDING FEDERALLY SPONSORED RESEARCH

This invention was made with government support under R01 ES019313, R01 MH094755, R01 AI123947, and R01 AI129788 awarded by the National Institute of Health. The government has certain rights in the invention.

TECHNICAL FIELD

The present disclosure relates to methods and systems for targeting immune CB1 receptors to provide a novel therapeutic modality to lessen Diet-Induced Obesity, and circumvent adverse side effects of CB1 antagonist or neuronal CB1 agonist treatment.

BACKGROUND

Nearly 40% of the world population is considered overweight or obese. The obesity pandemic is experiencing perpetual growth and robustly contributes to the global health burden due to many related complications that are triggered by chronic low-grade inflammation and consequent metabolic dysfunction. The endocannabinoid system (ECS) is a biological system that regulates a variety of obesity-related processes including appetite, inflammation, and metabolism. The system is comprised of cannabinoid receptors (CB) and their endogenous lipophilic ligands called endocannabinoids.

The two main cannabinoid receptors, CB1 and CB2, are G-protein coupled receptors that are expressed in various anatomical locations. CB1 expression is highly localized to the central nervous system where it is well known to mediate the psychotropic effects of delta-9-tetrahydrocannabinol (THC), and additionally expressed in peripheral metabolic tissues such as the liver, adipose tissue (AT), muscle, gastrointestinal (GI) tract, and in some immune cells. Thus, CB1 is heavily involved in regulation of energy metabolism, appetite, and food reward. Conversely, CB2 is largely expressed in the immune system where it modulates inflammatory pathways including pain and cytokine release. Various studies have shown immune-modulatory properties of CB2 agonists. Importantly, obesity is characterized by energy imbalance, chronic low-grade inflammation, and chronic ECS activation. Therefore, the ECS provides a mechanistic link between inflammation and metabolism during obesity that is not fully understood.

In the early 2000s, it was discovered that stimulation of CB1 promotes development of obesity. Blockade of CB1 reduced food intake in rodents and treatment of diet-induced obese (DIO) mice with the CB1 antagonist SR141716A led to amelioration of both obesity and metabolic impairments. Furthermore, CB1 knockout mice were shown to be resistant to development of high fat diet (HFD)-induced obesity and insulin resistance. Indeed, pharmacological blockade or genetic ablation of CB1 lessened appetitive behaviors, however additional appetite-independent metabolic benefits were observed indicating an increase in energy expenditure when CB1 signaling is impaired. Thus, CB1 became an attractive target for treatment of the ongoing obesity pandemic.

Unfortunately, due to adverse neuropsychiatric effects, SR141716A, also known as Rimonabant, was removed from the market. Despite this, research in the last decade has further characterized mechanisms of CB1 blockade-mediated metabolic improvements. Beneficial mechanisms of systemic CB1 antagonism beyond appetite regulation include decreasing obesity-associated inflammation through microRNA regulation of adipose tissue macrophages (ATM), increased brown adipose tissue thermogenesis, and increased insulin-dependent glucose utilization. Adipocyte-specific CB1 knockout also increases energy expenditure and promotes anti-inflammatory M2 ATM polarization, which highlights the importance of peripheral CB1 receptors in metabolic regulation. In addition, recent evidence shows that peripherally restricted CB1 antagonists can be used to treat obesity without central side effects, albeit, their anti-obesity effects are slightly less than that of central-acting CB1 antagonists.

In the current disclosure, we studied the role of CB1 in immune cells during DIO to determine whether anti-inflammatory effects of CB1 blockade were due to direct CB1 blocking in immune cells or a consequence of reduced obesity.

CB2 is the main cannabinoid receptor of the immune system and thus it is plausible anti-inflammatory effects of CB1 knockout or blockade may be attributed to increased CB2 signaling. However, previous studies on the role of CB2 in metabolism and obesity-induced inflammation have conflicting results. In one study, aged CB2−/− mice fed a normal chow diet had increased weight gain and elevated Cnr1 (CB1 gene) expression in white adipose tissue not associated with inflammation, while CB2−/− fed 60% HFD for 8 weeks had decreased weight gain and decreased adipose tissue inflammation versus WT mice.

In another study, treatment of 6-week 36% HFD-fed mice with the CB2 agonist JWH-133 for 15 days resulted in no change of body weight but increased adipose tissue inflammatory markers, while treatment with the CB2 antagonist AM630 reduced ATMs and adipose tissue inflammatory markers. In the same study, 15 weeks of 36% HFD feeding in CB2−/− mice resulted in less body weight and more insulin sensitivity versus WT mice, which coincided with decreased Cnr1 (CB1 gene) expression liver and adipose tissue. Another study with the CB2 agonist JWH-015, showed that 15 days of CB2 agonism in 20 week 21% HFD-fed DIO mice resulted in anorectic response and approximately 10% body weight loss, improved glucose tolerance, reduced adiposity, and increased lipolysis. All together, these studies show that CB2 plays a complex role in metabolic processes, which may be diet-dependent or involve interaction with CB1.

The endocannabinoid system regulates various physiological processes such as inflammation and metabolism, and is comprised of cannabinoid receptors, CB1 and CB2, as well as their ligands called endocannabinoids. Over-activation of CB1 is characteristic of obesity. While various cannabinoid receptor CB1 antagonists have been tested clinically to treat obesity, they were discontinued due to central nervous system toxicity. Accordingly, it is an object of the present disclosure to provide immune-targeting CB1 agonists that may lessen obesity and circumvent adverse side effects of non-specific CB1 antagonist therapy.

Citation or identification of any document in this application is not an admission that such a document is available as prior art to the present disclosure.

SUMMARY

The above objectives are accomplished according to the present disclosure by providing in a first embodiment, a method for treatment of endocannabinoid system dysfunction. The method may include targeting immune-specific CB1 receptors with an antagonist, activating immune-specific CB1 receptors via the antagonist, enabling CB1 signaling in immune cells to decrease neuroinflammation and induce weight loss. Further, treatment decreases ATM-mediated inflammation. Still, enabling CB1 signaling in immune cells decreases appetite. Yet further, the antagonist may comprise AM251, SR144528, SR141716A, JWH-133, Tocris 1343 and/or combinations of the above. Again, the antagonist may be administered at a dosage of between 5 mg/kg to 10 mg/kg. Still yet, the inflammation may be adipose tissue inflammation. Moreover, the method may reduce adipose tissue macrophage presence. Still again, hematopoietic CB1 may be targeted.

In a further embodiment, a method for treating dietary induced obesity is provided. The method may include targeting immune-specific CB1 receptors with an antagonist, activating immune-specific CB1 receptors via the antagonist, enabling CB1 signaling in immune cells to dampen neuroinflammation and induce weight loss. Still, treatment may decrease ATM-mediated inflammation. Yet again, enabling CB1 signaling in immune cells may decrease appetite. Yet further, the antagonist may comprise AM251, SR144528, SR141716A, JWH-133, Tocris 1343 and/or combinations of the above. Moreover, the antagonist may be administered at a dosage of between 5 mg/kg to 10 mg/kg. Still, the inflammation may be adipose tissue inflammation. Further yet, the method may reduce adipose tissue macrophage presence. More again, hematopoietic CB1 may be targeted.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

Figure 1:
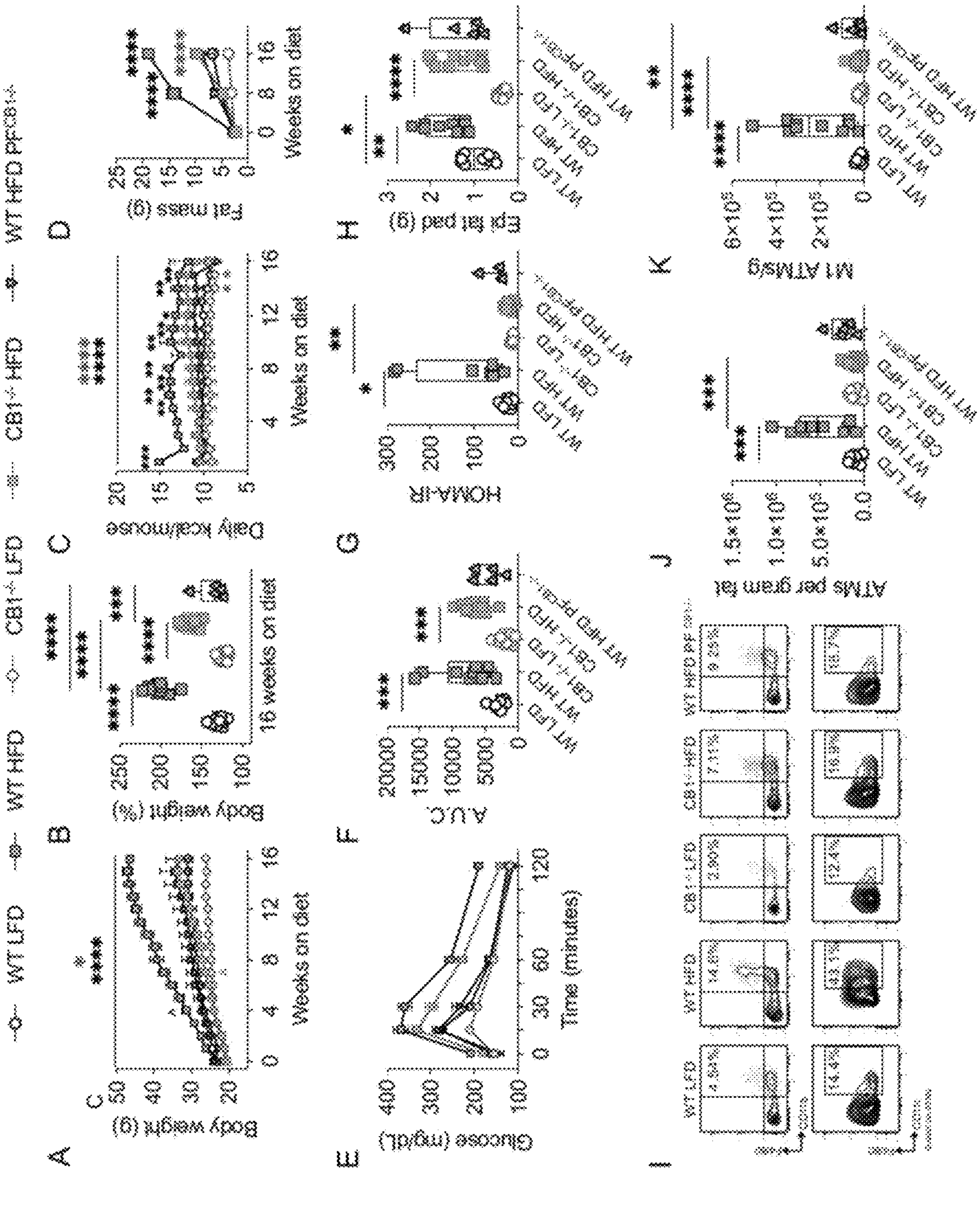
FIG. 1 shows Constitutive CB1 knockout reduces HFD-induced obesity and adipose tissue inflammation.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component (s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of a pharmaceutical formulation thereof such as any of the methods described in greater detail elsewhere herein.

Endocannabinoid system dysfunction and chronic inflammation promote obesity and its complications. Amelioration of diet-induced obesity (DIO) through blockade of cannabinoid receptor 1 (CB1) is associated with dampened inflammation, but the mechanisms are not clear. The current disclosure examines the role of CB1 signaling in immune cells during DIO. First, we showed constitutive CB1−/−, mice were resistant to high-fat diet (HFD)-induced weight gain and adipose tissue inflammation versus WT mice. Genetic and pharmacological inhibition of CB2 did not significantly alter DIO in our hands.

Next, we used bone marrow transplantation to generate chimeric mice that expressed functional CB1 in the entire body except hematopoietic cells, or only in bone marrow-derived cells. WT and CB1−/− hosts receiving autologous bone marrow were used as controls. Mice lacking functional CB1 in the entire body or only in non-hematopoietic cells were resistant to DIO, indicating that CB1 activation in non-immune cells is necessary for induction of HFD-induced adiposity. Interestingly, mice deleted for CB1 only in hematopoietic cells, resulted in recruitment of bone-marrow derived macrophages to the brain, accelerated weight gain, elevated appetite, increased glucose intolerance, and more inflammatory macrophages in visceral adipose tissue. Pharmacological inhibition of CB1 in CB2−/− DIO mice, as well as, CB2 agonist intervention in DIO mice suggested enhanced CB2 signaling may contribute to increased inflammation during immune CB1 deletion. Together these data identify opposing mechanisms of CB1 in hematopoietic and non-hematopoietic lineages during DIO. Thus, our study suggests functional CB1 signaling in immune cells is necessary to dampen HFD-induced microglia/macrophage-mediated neuroinflammation and reduce obesity.

Therefore, targeting immune CB1 receptors may constitute a novel therapeutic modality to lessen DIO, and circumvent adverse side effects of CB1 antagonist or neuronal CB1 agonist treatment.

Blocking CB1 receptors throughout the body promotes weight loss, although side effects on the central nervous system, such as depression and anxiety, have prevented approved use of these drugs in humans. The current disclosure reveals that while CB1 activation in non-immune cells promotes obesity, CB1 activation specifically in immune cells can dampen obesity. Thus, CB1 activation on immune cells may be used therapeutically to lessen obesity, prevent metabolic syndrome, and avoid adverse side effects of non-immune CB1 activation/inhibition.

Materials and Methods

Mice

Six- to 8-week-old male C57Bl/6J mice (JAX 000664), B6 CD45.1 (JAX 002014), and 18-week-old male C57Bl/6J mice fed either 60% kcal HFD (D12492, Research Diets) (JAX 380050), or purified 10% low-fat diet (LFD, D12450J, Research Diets) (JAX 380056) where indicated, for 12 weeks were obtained from The Jackson Laboratory and housed in a specific-pathogen-free facility. $CB1^{-/-}$ constitutive knockout mice were gifted from Dr. James Pickel (NIH National Institute of Mental Health Transgenic Core Facility, Bethesda, MD, USA). $CB2^{--}$ constitutive knockout mice were obtained from The Jackson Laboratory (JAX 005786). $CB1^{-/-}$ and $CB2^{-/-}$ mice were bred in-house and colonies maintained at the University of South Carolina School of Medicine animal facility. Mice were housed 3-5 mice per cage according to treatment group. In all experiments, each treatment group consisted of mice from multiple litters and cages. In some instances, mice were singly housed due to fighting. Pair feeding was performed by measuring the weight of HFD consumed each day, then administering that same weight of food to the Pair-fed group on the following day. At the conclusion of each study, mice were euthanized by overdose isoflurane inhalation. All experiments were performed in accordance with ethical standards approved by the University of South Carolina Institutional Animal Care and Use Committee.

Cannabinoid Receptor Agonist/Antagonist Administration

For DIO intervention studies, 12-week HFD-fed obese mice were stratified into treatment groups by equivalent mean DEXA fat mass, then treated with cannabinoid receptor agonists/antagonists, daily for 3-weeks. Compounds were purchased from Tocris, suspended in 0.1% Tween 80, and administered by oral gavage at the following doses: AM251 (10 mg/kg, Tocris 1117), SR144528 (10 mg/kg, Tocris 5039), JWH-133 (5 mg/kg, Tocris 1343). Experimental groups not receiving drug treatments were administered Vehicle (Veh) gavages.

Bone Marrow Transplantation

Six- to eight-week old male B6 CD45.1 (CB1 WT) or CB1−/− (expressing CD45.2) mice were lethally irradiated with a single dose of 900 cGy from a Cesium irradiator, then adoptively transferred intravenously with donor bone marrow cells. After 4 weeks of recovery, the mice were fed 60% HFD for 16 weeks.

Analytical Procedures

Body composition was measured by dual-energy x-ray absorptiometry (DEXA, LUNAR PIXImus) scanning as previously described. Body weight was monitored using an electronic gram scale with precision ±0.1 g. For glucose tolerance tests, mice were fasted for 5 hr, then fasting glucose was measured, immediately followed by oral gavage of 2 g/kg lean mass glucose (Sigma G7528). Blood glucose was measured 15 m, 30 m, 60 m and 120 m after glucose gavage by applying approximately 5 uL tail-tip blood to a glucose test strip in a glucometer (Contour Next, Bayer). To calculate a homeostatic model assessment of insulin resistance index (HOMA-IR), mice were fasted for 5 hr then blood glucose was measured from the tail-tip. Immediately following, mice were euthanized by overdose isoflurane inhalation and ~500 uL hepatic blood was collected and gently mixed with 15 uL 0.5M EDTA. To isolate plasma, blood was centrifuged 5000 RPM, 5 min, 4° C. and the top layer was collected and stored at −20° C. Insulin concentrations were measured in fasted plasma by ELISA (Invitrogen, EMINS). HOMA-IR index was calculated by the following equation [HOMA-IR=(fasting glucose×fasting insulin)/22.5].

Adipose Tissue Dissociation

Epididymal fat pads were excised, weighted, and dissociated using MACS adipose tissue dissociation kit and a gentleMACS dissociator according to manufacturer protocol (130-105-808, Miltenyi Biotec).

Isolation of Spleen Single-Cell Suspensions

Spleens were excised from euthanized mice and disrupted in 5 mL FACS buffer utilizing a Stomacher80 machine (Seward). Homogenates were filtered through a 70 um nylon mesh, pelleted, RBC-lysed, and washed in FACS buffer prior to flow cytometry staining.

Isolation of Brain Mononuclear Cells

Euthanized mice were perfused with 10 mL heparinized PBS then brains were harvested and dissociated using MACS neural tissue dissociation kit (P) and a gentleMACS dissociator according to manufacturer protocol (130-092-628, Miltenyi Biotec). The isolated cells were then RBC-lysed and spun through a 33% Percoll gradient (2000 RPM, 15 m, 25° C.) twice to remove myelin and other cellular debris. The isolated mononuclear cells (MNCs) were then washed in FACS buffer, counted, and plated $1\times10^6$ cells per well of a 12-well cell culture plate in complete RPMI-1640 medium containing 10% heat-inactivated FBS, 1% penicillin/streptomycin, 2 mM L-glutamine, 10 mM HEPES buffer, and 0.0002% ß-mercaptoethanol. The MNCs were cultured for 24 h to allow recovery of surface markers, then gently collected by scraping for flow cytometry staining.

Flow Cvtometry

For surface staining, cells were incubated with FcR-Blocker for 10 m followed by appropriate fluorochrome-conjugated antibodies for 30 m (CD45: clone 30-F11, CD45.1: clone A20, CD45.2: clone 104, CD11b: clone M1/70, F4/80: clone BM8, CD11c: clone N418). Stained cells were washed with FACS buffer then analyzed on a BD FACSCelesta flow cytometer. Data were analyzed and visualized with FlowJo v10.

Statistical Analysis

Statistical analyses were performed with GraphPad Prism Version 8.1.1 for Mac (GraphPad Software). Data presented are mean (±SEM) or box and whisker plots with individual points representing biological replicates. One-way ANOVA was used for multiple group analyses and two-way ANOVA was used for significance across multiple variables. Post hoc corrections were performed by Tukey and Sidak's multiple comparisons tests. A p value<0.05 was considered statistically significant.

Results

CB1 Regulates DIO Development and Associated Inflammation

To address the role of cannabinoid receptors in DIO-induced inflammation, 6-8-week-old male WT C57BL6 mice, constitutive $CB1^{-/-}$, and constitutive $CB2^{-/-}$ mice were fed 60% HFD or 10% LFD for 16 weeks. Consistent with previous reports, $CB1^{-/-}$ mice were resistant to HFD-induced weight gain, polyphagia, and adiposity, see FIG. A-D. Whereas $CB1^{-/-}$ mice developed HFD-induced hyperglycemia during glucose tolerance test, they maintained insulin sensitivity with low HOMA-IR, see FIG. 1 at E-G. The anti-obesity effects of CB1 deletion were largely due to reduced appetite as pair-fed controls (WT $HFD^{PF\ CB1-/-}$) displayed similarity to $CB1^{-/-}$ HFD mice, see FIG. 1 at A-G. FIG. 1 shows Constitutive CB1 knockout reduces HFD-induced obesity and adipose tissue inflammation.

Inflammation associated with obesity promotes development of adipose tissue insulin resistance and is largely driven by expansion of inflammatory adipose tissue macrophages (ATM). Therefore, we performed flow cytometry of stromal vascular fractions (SVF) of epididymal (Epi) fat after 16 weeks of purified diet. While CB1−/− mice experienced HFD-induced fat pad expansion, see FIG. 1 at H, they did not have HFD-induced infiltration of $CD11b^+F4/80^+$ATMs and inflammatory $CD11c^+$ M1 ATMs, see FIG. 1 at I and J. These data confirm that CB1 signaling regulates DIO development and adipose tissue inflammation.

We also evaluated DIO development and inflammation in $CB2^{-/-}$ mice because CB2 is the main cannabinoid receptor of the immune system. Previous publications have shown conflicting results of CB2 inhibition in DIO. In our hands, we observed no significant changes in 60% HFD-induced DIO development or adipose tissue inflammation in $CB2^{-/-}$ versus WT mice, see FIG. 6 at A-K. Furthermore, we treated 12-week HFD-fed DIO mice with the CB2 antagonist SR144528 (10 mg/kg) for 21 consecutive days and observed no changes in body weight, food intake, glucose tolerance, or adipose tissue inflammation versus vehicle-treated mice, see FIG. 6 at L-R. Thus, we concluded CB1, but not CB2, may be the primary cannabinoid receptor regulating DIO-induced inflammation.

Figure 6:
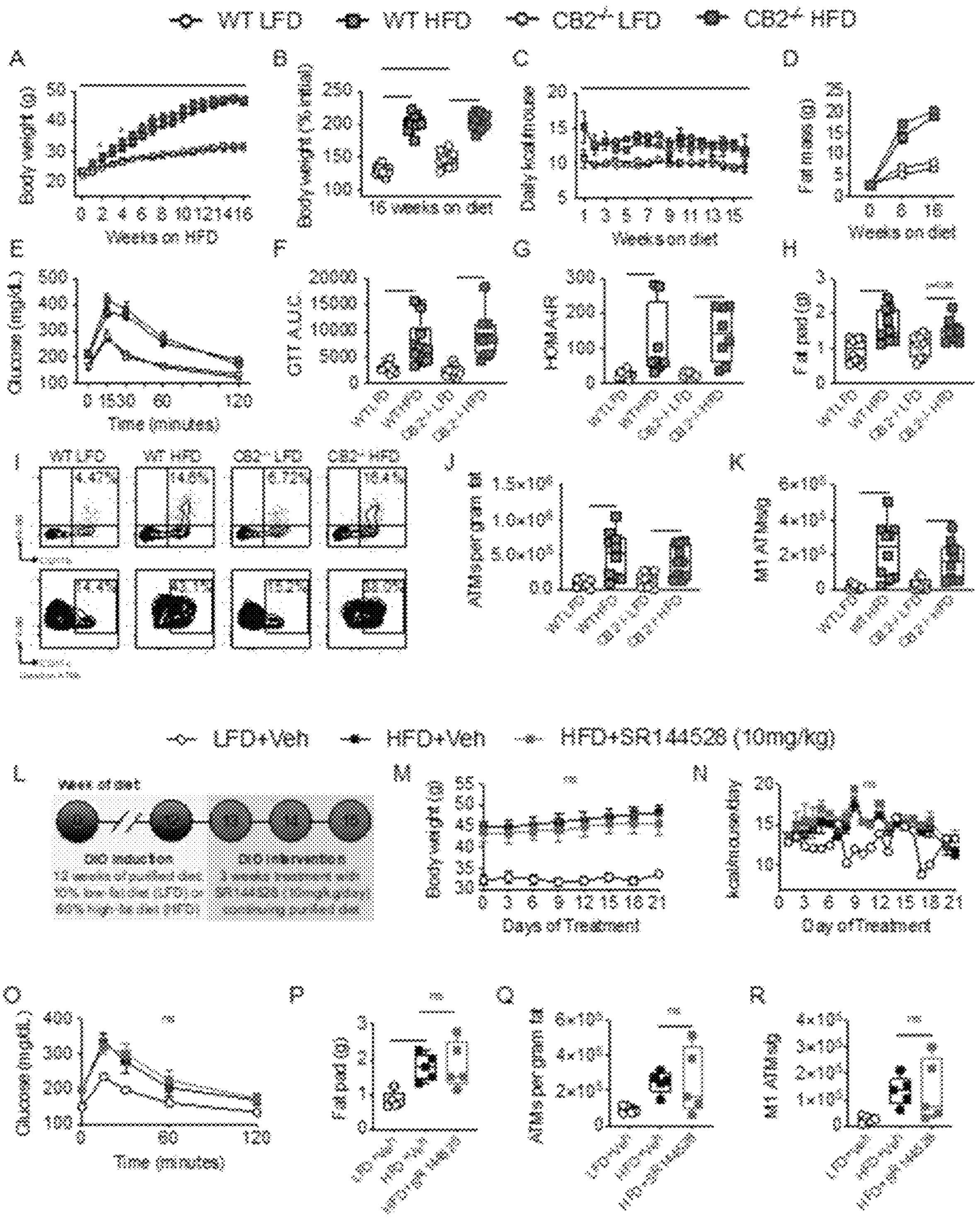
FIG. 6 shows CB2 knockout or inhibition does not alter HFD-induced inflammation.

FIG. 6 shows CB2 knockout or inhibition does not alter HFD-induced obesity or inflammation. For A-K, 6-8-weeks-old WT or constitutive CB2 knockout mice were fed LFD or HFD for 16 weeks. For L-R, DIO mice were treated with the CB2 antagonist SR144528 (10 mg/kg) or vehicle for 21 consecutive days. FIG. 6 shows at: A) Body weight growth curves during 16 weeks of diet; B) endpoint body weight expressed as percent of starting weight, C) weekly means of daily calorie intake per mouse; D) DEXA fat mass at 0, 8, and 16 weeks on diet; E) oral GTT performed during the $16^{th}$ week of diet; F) GTT area under the curve (A.U.C.); G) HOMA-IR insulin resistance index after 16 weeks on diet; H) epididymal fat pad wet weight; I) representative flow cytometry contour plots of epididymal $CD11b^+F4/80^+$ ATMs and ATM-gated $CD11c^+$ M1 ATMs; J) quantification of ATMs per gram of epididymal fat; K) quantification of M1 ATMs per gram of epididymal fat; L) DIO intervention model timeline; M) body weight during 21 days of treatment; N) daily calorie intake per mouse; O) oral GTT during the $3^{rd}$ week of treatment; P) epididymal fat pad wet weight; Q) $CD11b^+F4/80^+$ ATMs per gram of fat; and R) $CD11c^+$ M1 ATMs per gram of fat. Data are mean+/−SEM or box and whisker plots with individual points representing biological replicates. For A-K, N=10 mice/group except N=2 cages for C. For L-R, N=5 mice/group except N=2 cages for N. *p<0.05, p<0.01, *p<0.001, ****P<0.0001 by one- or two-way ANOVA with Tukey post-hoc tests.

CB1 Deficiency in Immune Cells Potentiates DIO.

Because we observed associations between CB1 deletion, DIO resistance, and absence of adipose tissue inflammation, we next aimed to determine whether CB1 deletion directly reduced HFD-induced inflammation and consequently DIO development, or if reduced inflammation was an indirect consequence of the reduced obese phenotype. Thus, to study the direct contribution of CB1 signaling in immune cells during DIO, we generated chimeric mice that expressed functional CB1 in the entire body except hematopoietic cells (CB1−/−→WT), or only in hematopoietic cells (WT→CB1−/−). Six- to 8-week-old male B6 CD45.1 (CB1 WT) and CB1−/− (CB1 KO expressing CD45.2) were lethally irradiated and adoptively transferred with viable donor bone marrow. WT and CB1−/− hosts receiving autologous bone marrow were used as controls. After recovery, mice were fed HFD for 16-weeks. We confirmed chimerism by staining splenocytes for CD45 and CD45.1/CD45.2 alleles, see FIG. 7 at A and B.

Figure 2:
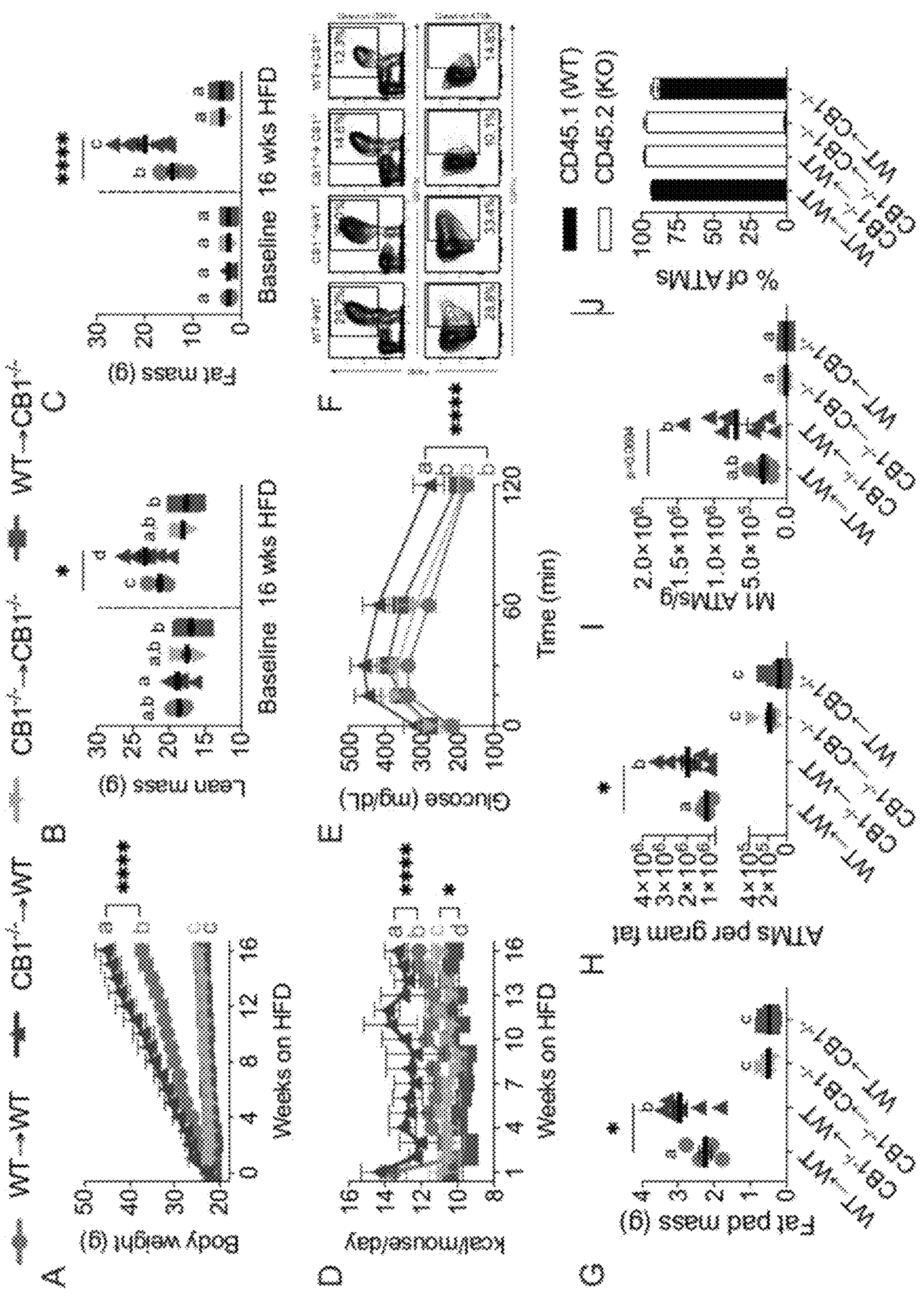
FIG. 2 shows CB1 knockout in hematopoietic cells worsens HFD-induced obesity and adipose tissue inflammation.

Mice lacking functional CB1 in the entire body or only in non-hematopoietic cells were resistant to HFD-induced weight gain and adiposity, indicating that CB1 activation in non-immune cells is necessary for induction of HFD-induced adiposity (FIG. 2 at A-C). Interestingly, mice deleted for CB1 only in hematopoietic cells had accelerated weight gain, higher lean mass, and higher fat mass than WT controls, suggesting that CB1 activation regulates exacerbation of DIO in susceptible hosts (FIG. 2 at A-C). Weekly monitoring of food intake also showed both groups of mice deleted for CB1 in immune cells, regardless of the host genotype, had greater appetites than control mice containing WT immune cells (FIG. 2 at D). Furthermore, WT mice lacking CB1 in immune cells displayed elevated glucose intolerance by glucose tolerance test (FIG. 2 at E). FIG. 2 shows CB1 knockout in hematopoietic cells worsens HFD-induced obesity and adipose tissue inflammation.

Figure 7:
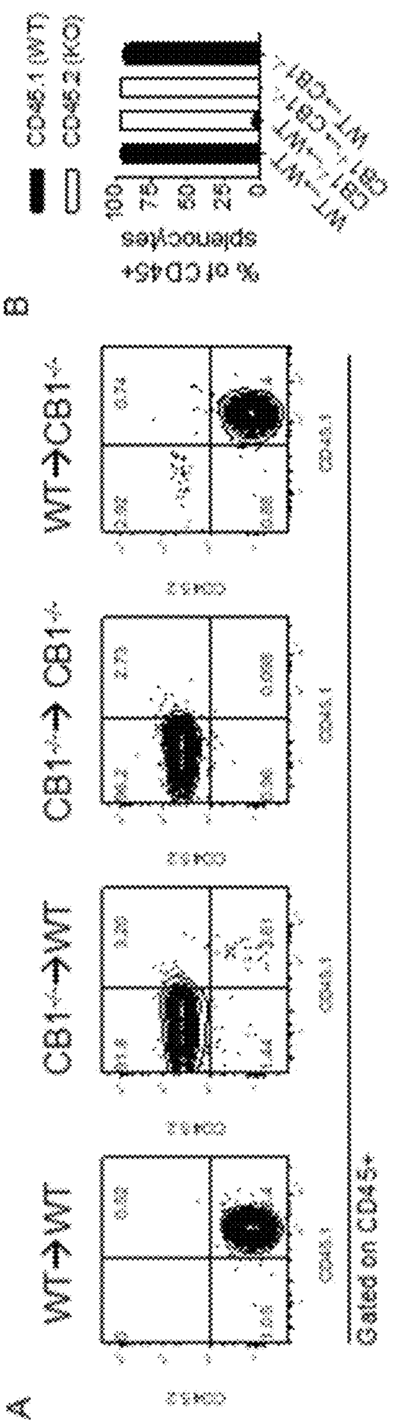
FIG. 7 shows validation of bone marrow reconstitution in chimeric mice.

FIG. 7 shows validation of bone marrow reconstitution in chimeric mice. Chimeric mice were generated by bone marrow transplantation as described vis-a-vis FIG. 2. After 16 weeks of HFD, spleens were harvested and stained for CD45, CD45.1, and CD45.2 to confirm immune system reconstitution by donor cells. FIG. 7 shows at: A) representative flow cytometry contour plots of CD45+ gated splenocytes; and at B) percentages of CD45+ splenocytes expressing CD45.1 (CB1 WT) and CD45.2 (CB1 KO).

In addition to a worsened obese phenotype, mice deficient for CB1 only in immune cells had increased ATM-mediated inflammation, with higher fat pad mass, and more ATMs per gram of fat than WT mice (FIG. 2 at F-H). Abundance of CD11c+M1 ATMs also trended higher in these mice (FIG. 2 at I). Still, mice deficient for CB1 in the whole body and only in non-immune cells, were resistant to HFD-induced ATM inflammation, likely due to their decreased obese phenotype (FIG. 2 at F-I). CD45.1/CD45.2 staining of ATMs confirmed they were infiltrating bone-marrow derived cells (FIG. 2 at J).

Immune CB1 Receptors Regulate Myeloid Neuroinflammation and Appetite

Figure 3:
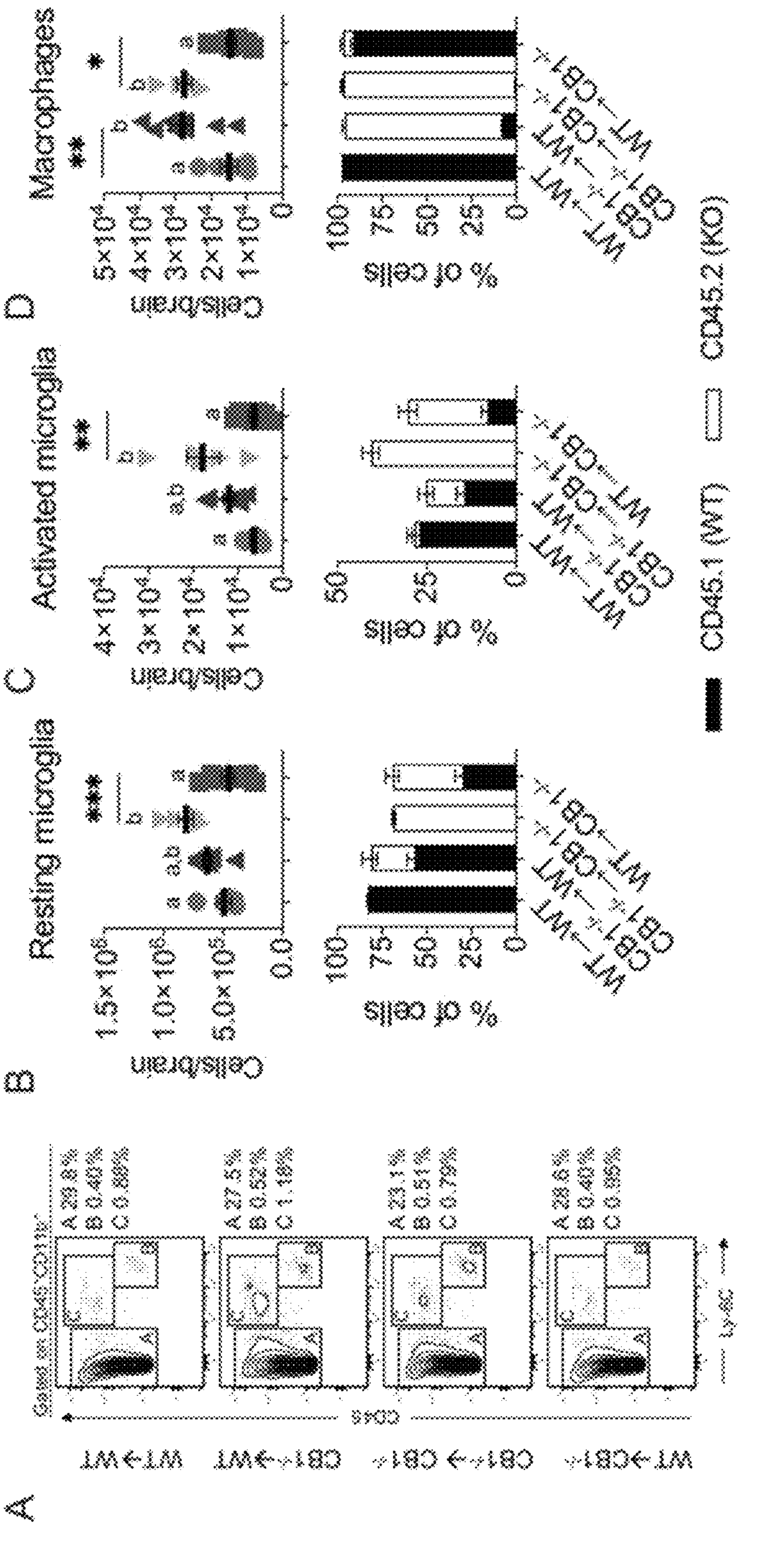
FIG. 3 shows Immune CB1 deletion promotes myeloid neuroinflammation.

Together, the current disclosure shows associations between HFD-induced weight gain, adipose tissue inflammation, and glucose intolerance. However, both groups of mice lacking $CB1^{-/-}$ in immune cells also had elevated appetite versus their respective host control. To identify a potential mechanism of immune CB1 in appetite regulation, we next performed flow cytometry of brain mononuclear cells (MNC) for microglia and macrophages because inflammatory microgliosis and bone-marrow derived myeloid recruitment to the hypothalamus promotes diet-induced hyperphagia and weight gain. We identified three populations of myeloid cells in brain MNCs, which were defined as CD45+CD11b+Ly-$6C^{-}$ resting microglia, $CD45^{lo}$CD11b+ Ly-$6C^{hi}$ activated microglia, and $CD45^{hi}$CD11b+Ly-$6C^{+}$ infiltrating macrophages, see FIG. 3 at A. Quantification of these populations per brain and CD45.1/CD45.2 staining showed that mice completely deleted for CB1 had elevated abundance of all three populations, see FIG. 3 at B-D. Furthermore, WT mice given $CB1^{-/-}$ bone marrow had increased infiltration of bone-marrow derived macrophages, See FIG. 3 at D. Microglia numbers trended higher in these mice but was not significant, likely due to presence of irradiation-resistant WT resident microglia, FIG. 3 and B-C. Together these data demonstrated loss of CB1 in immune cells promotes myeloid neuroinflammation contributing to increased appetite, and thus increased DIO in susceptible hosts.

Figure 4:
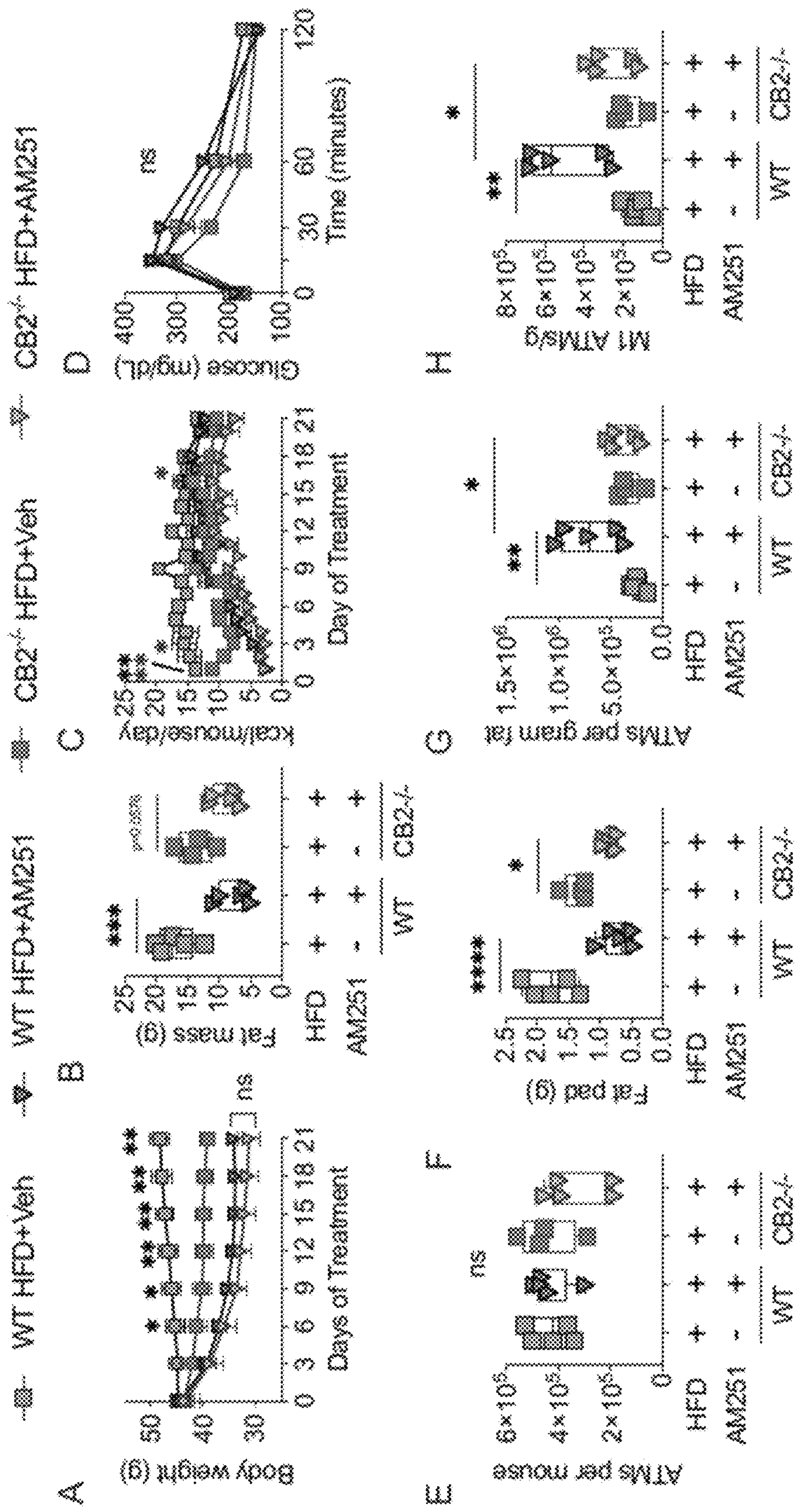
FIG. 4 shows CB1 antagonist DIO intervention promotes CB2-independent weight loss and reduced appetite but promotes CB2-dependent ATM retention.

CB1 Blockade Reverses DIO But Sustains ATM iNflammation During Weight Loss Via a CB2-Dependent Mechanism To determine if pro-inflammatory effects of CB1 deficiency in immune cells was perhaps due to increased endocannabinoid signaling through CB2, we next treated 12-week HFD-fed WT and $CB2^{-/-}$ DIO mice with the CB1 antagonist AM251 (10 mg/kg) for 21 consecutive days. AM251 treatment resulted in weight loss, reduced adiposity, and suppressed appetite, independent of CB2, see FIG. 4 at A-C). Treatment did not alter glucose tolerance, see FIG. 4 at D. Flow cytometry analysis of epididymal ATMs showed ATM numbers remained constant after 3 weeks of treatment, see FIG. 4 at E. However, AM251 reduced fat pad mass and thus ATMs and M1 ATMs per gram of adipose tissue were greater in AM251-treated WT mice but not in $CB2^{-/-}$ mice, see FIG. 4 at F-H. These data suggested that enhanced CB2 signaling contributes to persistence of ATM inflammation.

Figure 5:
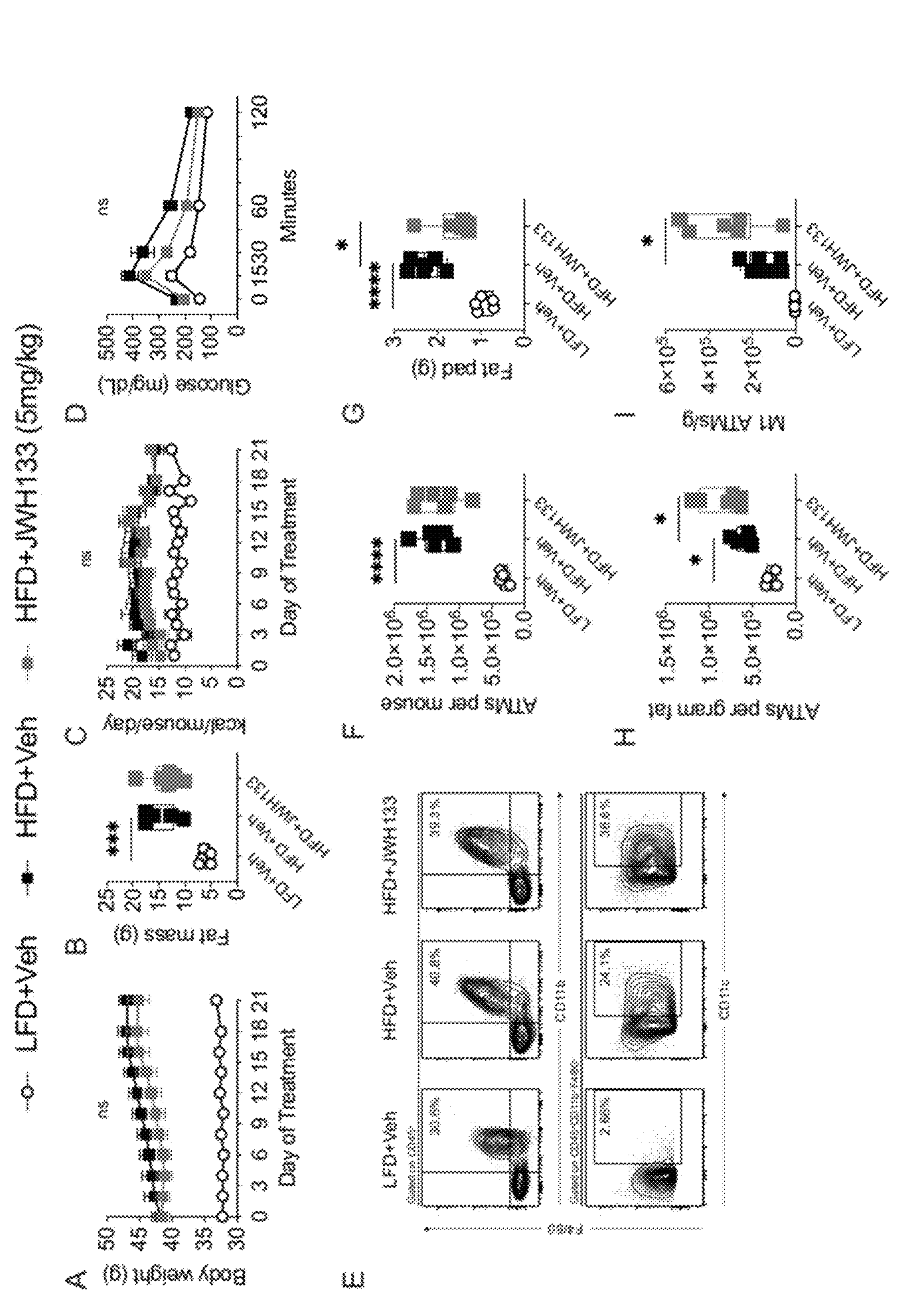
FIG. 5 CB2 agonist treatment of DIO mice enhances ATM abundance.

To further test the role of CB2 activation in ATM-mediated inflammation, we treated 12-week HFD-fed DIO mice with the CB2 agonist JWH-133 (5 mg/kg) for 21 consecutive days. CB2 agonist treatment did not significantly alter body weight, fat mass, food intake, or glucose tolerance, see FIG. 5 at A-D). Similar to CB1 blockade, CB2 activation promoted persistence of total ATMs, FIG. 5 at E-F. However, JWH-133 treatment promoted fat pad loss and thus increased numbers of ATMs and M1 ATMs per gram of fat, see FIG. 5 G-I. Together these data show that CB2 activation contributes to ATM-retention during fat shrinkage.

Discussion

The anti-obesity and anti-inflammatory effects of CB1 blockade have been well documented, yet studies on the direct effects of CB1 blockade in the immune system are limited. Here we show that CB1 signaling in non-immune cells regulates susceptibility to HFD-induced obesity, while CB1 signaling in immune cells controls exacerbation of DIO-induced inflammation. Indeed, previous studies have shown whole-body deletion of CB1 as well as conditional deletion of CB1 in adipocytes and neuronal cells promotes resistance to DIO. Thus, CB1 signaling in non-immune cells contributes to obesity onset. We have also shown 4 weeks' treatment of DIO mice with the CB1 antagonists SR141716A and AM251, promotes rapid and sustained weight loss associated with decreased adipose tissue inflammation. Whether these anti-inflammatory observations were a cause or effect of decreased obese phenotype was an unanswered question.

The current disclosure demonstrates chimeric mice lacking CB1 only in hematopoietic cells actually promoted inflammation and worsened obesity. Additionally, 3-week treatment of DIO mice with AM251 promoted persistent abundance of ATMs and $CD11c^{+}$ ATMs in visceral adipose tissue. This pro-inflammatory effect of 3-weeks' CB1 blockade differs from previous studies with 4-weeks' CB1 blockade. However, a previous study on lipolysis induced by 3-week dietary change from HFD to normal chow resulted in stable abundance of ATMs and $CD11c^{+}$ ATMs but with decreased inflammatory profile. Interestingly, ATM numbers decreased towards normal after 5 weeks in this study. Therefore, differences in ATM abundance after 3-weeks' and 4-weeks' CB1 blockade suggests that fat pad loss precedes emigration of ATMs from adipose tissue. Thus, the anti-inflammatory effects of 4-week CB1 blockade were likely a consequence of reduced fat pad mass induced by CB1 antagonist action in non-immune cells.

We also studied the involvement of enhanced CB2 signaling in regulating inflammation during CB1 blockade. Loss of ATM persistence during 3-weeks' CB1 blocking in CB2 deficient mice suggested that CB2 signaling was needed to retain ATMs. Furthermore, augmented CB2 signaling by 3-weeks' treatment of DIO mice with JWH-133 resulted in stable abundance of ATMs but more per gram of fat due to fat pad shrinkage. Similarly, Deveaux et al. showed 15 day treatment of 6-week HFD-fed DIO with JWH-133 potentiated obesity and increased white adipose tissue expression of Emr1, encoding the macrophage marker F4/80. The current disclosure suggests CB1 blocking in immune cells increases CB2-induced inflammation.

A driving force for beneficial effects of CB1 deletion in DIO rely on reduced appetite. Herein, we show constitutive deletion of CB1 promotes resistance to DIO, consistent with previous literature. Contrary to previous publications with CB1 antagonists, the anti-obesity effects of CB1 deletion were largely due to reduced calorie intake because our pair-fed controls displayed similar DIO development to $CB1^{-/-}$ HFD mice. However, it is noteworthy that anti-obesity effects observed in our pair-fed control group could have been in part due to intermittent fasting because this group consumed all supplied food each day and likely experienced significant amounts of time without food access between daily feedings. The anti-obesity effects of intermittent fasting have been previously described, thus, controlling for appetite and calorie intake was a challenge in our model.

Interestingly, the current disclosure found absence of CB1 in immune cells promoted elevated appetite, perhaps via a CB2-independent mechanism because enhanced CB2 signaling did not promote hyperphagia. Therefore, we interrogated encephalitogenic myeloid cells because HFDs activate hypothalamic inflammation, which in turn contributes to energy imbalance and impaired insulin signaling. We found that CB1 deficiency in immune cells activated microgliosis and infiltrating macrophages in the brain. Indeed, a limitation of our study was isolating immune cells from the entire brain instead of only the hypothalamus. However, obesity is known to induce hypothalamic inflammation, thus, differences we observed are likely to be representative of hypothalamic immune cells.

Together, the current disclosure suggests non-functional CB1 signaling in microglia and encephalitogenic macrophages contributes to neuroinflammation and, consequently, increased appetite. Another possible explanation could be that non-functional CB1 signaling in encephalitogenic myeloid cells increases endocannabinoid signaling through neuronal CB1 receptors to increase appetite. Future studies targeting microglial and macrophage CB1 receptors could shed light on therapeutic potential of selective immune-acting CB1 agonists for treating obesity by reducing appetite.

Suitable CB1 receptor antagonists may include AM-251, AM-6545, Cannabigerol, Drinabant, GAT 100, Ibipinabant, JD5037, JWH-193, LY-320, LY-135, MK-9470, NESS-0327, O-2050, Org 27569, Otenabant, PF-514273, PiplSB, Pregnenolone, PSNCBAM-1, Rimonabant, Rosonabant, Surinabant, Taranabant, Tetrahydrocannabivarin, TM-38837, VCHSR, Virodhamine, and/or combinations of the above or other antagonists described herein.

In conclusion, the current disclosure identifies hematopoietic CB1 as a novel therapeutic target for DIO. Combinatorial analysis of constitutive knockouts, chimeric mice, and pharmacological interventions identified non-hematopoietic CB1 receptors as initiators of HFD-induced weight gain, but hematopoietic CB1 receptors as restrictors of DIO. Of note, chronic administration of the psychoactive CB1 agonist THC in DIO mice reduces HFD-induced polyphagia, weight gain, and adiposity. Additionally, chronic Cannabis users have reduced obesity rates. Moreover, numerous studies from our laboratory have shown anti-inflammatory effects of THC. Thus, chronic CB1 agonism may reduce inflammation contributing to reduced appetite and obesity. Therefore, activating immune-specific CB1 receptors may constitute a novel anti-inflammatory therapeutic to lessen DIO and circumvent adverse neuropsychiatric and psychotropic side effects of CB1 antagonist or neuronal CB1 agonist treatments, respectively.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth. In a further embodiment the disclosure provides blocking immune-specific CB1 receptors via the antagonist so that the endocannabinoids won't be able to activate CB1.

What is claimed is:

1. A method for treatment of endocannabinoid system dysfunction comprising:

treating diet induced obesity in a subject via reducing appetite via;

selectively targeting immune-specific cannaboid receptor CB1 in immune cells via delivery of an agonist to the immune cells; and selectively activating immune-specific cannaboid receptor CB1 in the immune cells via the agonist;

enabling cannaboid receptor CB1 signaling in the immune cells to:

decrease neuroinflammation; and induce weight loss.

2. A method for treating dietary induced obesity comprising:

treating diet induced obesity in a subject via;

selectively targeting immune-specific cannaboid receptor CB1 in immune cells via delivery of an agonist to the immune cells; and selectively activating immune-specific cannaboid receptor CB1 in immune cells via the agonist;

enabling cannaboid receptor CB1 signaling in immune cells to:

dampen neuroinflammation; and induce weight loss.

3. A method for treatment of endocannabinoid system dysfunction comprising:

treating diet induced obesity in a subject via reducing appetite via;

selectively targeting hematopoietic-specific cannaboid receptor CB1 in hematopoietic cells via delivery of an agonist to the hematopoietic cells; and selectively activating hematopoietic-specific cannaboid receptor CB1 in the hematopoietic cells via the agonist;

enabling cannaboid receptor CB1 signaling in the hematopoietic cells to:

decrease neuroinflammation; and induce weight loss.

4. A method for treating dietary induced obesity comprising:

treating diet induced obesity in a subject via;

selectively targeting hematopoietic-specific cannaboid receptor CB1 in hematopoietic cells via delivery of an agonist to the hematopoietic cells; and selectively activating hematopoietic-specific cannaboid receptor CB1 in hematopoietic cells via the agonist;

enabling cannaboid receptor CB1 signaling in hematopoietic cells to:

dampen neuroinflammation; and induce weight loss.

* * * * *